United States Patent [19]

Keil

[11] 4,265,878

[45] May 5, 1981

[54] ANTIPERSPIRANT STICK COMPOSITIONS

[75] Inventor: Joseph W. Keil, Midland, Mich.

[73] Assignee: Dow Corning Corporation, Midland, Mich.

[21] Appl. No.: 46,591

[22] Filed: Jun. 7, 1979

[51] Int. Cl.³ .................... A61K 7/38; A61K 31/695
[52] U.S. Cl. .................... 424/68; 424/DIG. 5; 424/65; 424/66; 424/67; 424/184
[58] Field of Search ............................ 424/68, DIG. 5

[56] References Cited

U.S. PATENT DOCUMENTS

| | | | |
|---|---|---|---|
| 4,049,792 | 9/1977 | Elsnau | 424/68 X |
| 4,053,581 | 10/1977 | Pader et al. | 424/66 X |
| 4,065,564 | 12/1977 | Miles, Jr. et al. | 424/66 |
| 4,073,880 | 2/1978 | Pader et al. | 424/68 X |
| 4,110,428 | 8/1978 | Kuhn et al. | 424/68 X |
| 4,126,679 | 11/1978 | Davy et al. | 424/68 X |

FOREIGN PATENT DOCUMENTS

| | | | |
|---|---|---|---|
| 1100882 | 3/1961 | Fed. Rep. of Germany | 424/358 |
| 1251467 | 10/1967 | Fed. Rep. of Germany | 424/68 |
| 2365219 | 7/1974 | Fed. Rep. of Germany | 424/68 |
| 656748 | 8/1951 | United Kingdom | 424/68 |
| 843865 | 8/1960 | United Kingdom | 424/68 |
| 880261 | 10/1961 | United Kingdom | 424/68 |
| 1536222 | 12/1978 | United Kingdom | 424/68 |

*Primary Examiner*—Dale R. Ore
*Attorney, Agent, or Firm*—George A. Grindahl

[57] ABSTRACT

Antiperspirant stick compositions are described which comprise an aqueous solution of an astringent dispersed in a solid matrix comprising a volatile, water-insoluble liquid; a polydiorganosiloxane-polyoxyalkylene copolymer; a solid alkanoic acid; a waxy ester; and optionally containing a solid alkanol. A preferred embodiment comprises an aqueous solution of aluminum chlorhydrate dispersed in a solid matrix comprising cyclopolydimthylsiloxanes as the volatile liquid. These compositions are stable to separation in the molten state and provide non-leaking sticks of controllable softness when solidified by cooling.

5 Claims, No Drawings

ANTIPERSPIRANT STICK COMPOSITIONS

BACKGROUND OF THE INVENTION

This invention relates to antiperspirant stick compositions of the so-called dry-feeling type comprising an emulsion of an aqueous solution of an astringent in a solid matrix comprising a volatile, water-insoluble liquid and having stability relative to separation in the molten state and stability relative to leaking in the solid state.

Antiperspirant compositions are well known in the cosmetic art. These compositions are formulated as aerosols, gels, sticks, creams, pump sprays and lotions and comprise an astringent, typically comprising one or more zirconium salts and/or aluminum salts, in various forms such as a dry, impalpable powder, an alcohol solution or an aqueous solution. Of these various forms of astringents the aqueous solution is known to be the most effective antiperspirant.

However, an antiperspirant composition having water as the continuous phase, such as an aqueous solution of an astringent, or an oil-in-water type emulsion thereof, is less desirable than a composition comprising a dry powder or an alcohol solution thereof because it tends to feel wet when applied to the human skin and to go through a tacky state during the drying period after application.

Gee et al., U.S. Pat. No. 4,122,029 have disclosed water-in-oil type compositions having broad utility and comprising a polydiorganosiloxane-polyoxyalkylene copolymer and a water-in-oil type surfactant. When formulated as an antiperspirant emulsion of an aqueous solution of an astringent, such as aluminum chlorhydrate, emulsified in a volatile, non-aqueous continuous phase the compositions of Gee et al. have a desirable dry feeling when applied to the human skin and do not exhibit the wet-and-tacky effect noted above.

Keil, in a U.S. Patent Application entitled "Antiperspirant Emulsion Compositions", filed on even date herewith and assigned to the assignee of this application, discloses new antiperspirant compositions which have improved efficacy compared to the antiperspirants of Gee et al. and still do not exhibit the wet-and-tacky effect.

Although water-in-oil type antiperspirant compositions such as those of Gee et al. and of Keil, may be formulated in several forms, such as lotions, gels and sprays using well-known methods, the preparation of stick-forming compositions therefrom which do not separate in the molten state and which solidify to a non-leaking stick has not been entirely successful using the conventional teachings of the art.

Cosmetic sticks, such as antiperspirant sticks, are typically prepared by first preparing a molten, solidifiable composition comprising all components and thereafter casting the molten composition in the desired shape and/or dispenser. When the molten composition is an emulsion successful completion of this process requires that the emulsion be stable against separation. In addition, the resulting stick must not leak, i.e. lose liquid. The usual mixing of singular gelling agents with the compositions of Gee et al. and of Keil do not satisfy these requirements.

SUMMARY OF THE INVENTION

It is an object of this invention to provide non-leaking antiperspirant stick compositions of the water-in-oil type. It is a further object of this invention to provide antiperspirant emulsion compositions of the water-in-oil type which are stable in the molten state.

The present invention achieves these objects, and others which will be obvious upon consideration of this disclosure, by mixing a stick-forming mixture of components consisting essentially of a solid alkanoic acid, such as stearic acid, and a waxy ester, such as spermaceti wax, optionally containing up to three parts by weight of a solid alkanol, such as stearyl alcohol, for every one part of waxy ester, with water-in-oil type antiperspirant emulsion components comprising a polydiorganosiloxane-polyoxyalkylene copolymer. The solid alkanoic acid is used in sparing amounts to control crystallinity in, and thus prevent leaking of, the antiperspirant stick while the waxy ester is used in sufficient amounts to confer stability to the molten composition.

While not wishing to be limited by theory I believe that my invention is successful because the solid alkanoic acid and waxy ester, in addition to providing the solidifying action for stick formation, also serve additional functions. I believe that the solid alkanoic acid serves as an auxillary water-in-oil type surfactant while the waxy ester has better compatibility with the primary water-in-oil type surfactant, i.e. the polydiorganosiloxane-polyoxyalkylene copolymer, and the volatile liquid than do the solid alkanols usually used in stick formulations.

DETAILED DESCRIPTION OF THE INVENTION

This invention relates to antiperspirant stick compositions consisting essentially of (a) 30 to 60 parts by weight of an aqueous solution of an astringent as a discontinuous phase dispersed in a solid matrix consisting essentially of (b) 18 to 30 parts by weight of a volatile liquid having a normal boiling point of less than 250° C. selected from the group consisting of methylsiloxane fluids having the average unit formula

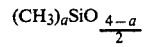
$$(CH_3)_a SiO_{\frac{4-a}{2}}$$

wherein a has an average value of from 2 to 3, inclusive, and paraffinic hydrocarbon fluids, (c) 1 to 5 parts by weight of at least one solid alkanoic acids having at least 12 carbon atoms per molecule, (d) 1 to 5 parts by weight of a polydiorganosiloxane-polyoxyalkylene copolymer containing at least one polydiorganosiloxane segment consisting essentially of

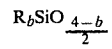
$$R_b SiO_{\frac{4-b}{2}}$$

siloxane units wherein b has a value of from 0 to 3, inclusive, there being an average value of approximately 2 R radicals per silicon for all siloxane units in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8 and (e) 20 to 30 parts by weight of a component selected from the group consisting of at least one waxy ester and a mixture of one part by weight of at least one waxy ester with up to 3 parts by weight of at least one solid alkanol having at least 12 carbon atoms per molecule, the total of (a) plus (b) plus (c) plus (d) plus (e) being 100 parts by weight.

Component (a) is an aqueous solution of any astringent antiperspirant agent. Examples of well-known astringents include the aluminum, hafnium and zirconium salts, such as zirconyl hydroxide halides, zirconium-aluminum complex salts, aluminum chloride, sodium aluminum lactate, basic aluminum halides such as $Al_2(OH)_5Cl$, aluminum bromide and the several water, alcohol or glycine complexes thereof.

The amount of astringent that is dissolved in water to form component (a) may vary widely and is not critical; however, certain practical limitations exist. On the one hand an efficacious antiperspirant composition should contain sufficient astringent to provide sweat reduction, although compositions containing less astringent are useful as personal care compositions. Preferably the antiperspirant compositions comprises approximately 15 to 30 weight percent astringent. On the other hand it is desirable to maximize the amount of water in the antiperspirant formulation without negating utility, for obvious economic reasons. Depending on the particular astringent that is used, component (a) may vary in concentration from as little as one part by weight astringent per three parts by weight water up to a saturated aqueous solution of the astringent. Considering economy and efficacy, a particularly useful component (a) is an aqueous solution of aluminum chlorhydrate consisting of equal weight portions of water and aluminum chlorhydrate.

The volatile liquid (b) is a fluid selected from the group consisting of methylsiloxane fluids, paraffinic hydrocarbon fluids and their mixtures, further detailed below. To be suitable as a volatile fluid for an antiperspirant composition component (b) should have a normal, i.e. atmospheric pressure, boiling point of less than 250° C. Methylsiloxane fluids and paraffinic hydrocarbon fluids meeting this parameter also typically have a viscosity at 25° C. of less than 10 millipascal-seconds (mPa.s). One millipascal-second equals one centipoise. To avoid an excessive cooling effect for the user of the compositions of this invention it is preferred that at least a portion of the volatile liquid have a normal boiling point of from 100° to 200° C.

The volatile methylsiloxane fluid (b) has the average unit formula

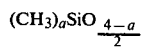

where a has an average value of from 2 to 3 and consists of siloxane units selected from the group consisting of $(CH_3)_3SiO_{1/2}$, $(CH_3)_2SiO_{2/2}$, $CH_3SiO_{3/2}$ and $SiO_{4/2}$ units. Preferably the volatile methylsiloxane fluid consists essentially of dimethylsiloxane units, and optionally, trimethylsiloxane units. Of particular value as volatile liquid (b) are the cyclic siloxanes of the general formula $\{(CH_3)_2SiO\}_x$ and the linear siloxanes of the general formula $(CH_3)_3SiO\{(CH_3)_2SiO\}_ySi(CH_3)_3$, and their mixtures, wherein x is an integer of from 3 to 6 and y is an integer of from 0 to 4. A highly preferred methylsiloxane fluid is a mixture of said cyclic siloxanes wherein a major portion is tetramer (X=4).

Paraffinic hydrocarbon fluids suitable for use as component (b) in these compositions correspond to the average unit formula $C_nH_{2n+2}$, in the well-known manner, wherein n is an integer having a value of less than 15. A particularly suitable paraffinic hydrocarbon fluid is a high-purity isoparaffin available from Exxon Corporation as Isopar ™.

The volatile fluid, in addition to being a methylsiloxane fluid or a paraffinic hydrocarbon fluid, may be any mixture of said methylsiloxane fluid and said paraffinic fluid, such as a mixture of octamethylcyclotetrasiloxane and hexane or decamethylcyclopentasiloxane and hexane or a mixture of two or more of said cyclosiloxanes and one or more paraffins.

Methylsiloxane fluids and paraffinic hydrocarbons, suitable for use as volatile fluid (b) in the compositions of this invention, are well known in the chemical and polymer arts; many are commerically available.

Component (c) is a stick-stabilizing component selected from the group consisting of solid alkanoic acids having at least 12 carbon atoms per molecule. By solid it is meant that the alkanoic acid has a melting point above 20° C. and preferably above 40° C.

Component (c) is preferably selected from the group of solid alkanoic acids which are widely used in the cosmetic art, such as palmitic acid and stearic acid. Component (c) may be a single alkanoic acid or a mixture of two or more alkanoic acids and may be of synthetic and/or natural origin.

It should be noted that although many alkanoic acids having 12 or more carbon atoms can be prepared in essentially pure form, they are usually used in the cosmetic art as mixtures. For example, stearic acid is predominantly $CH_3(CH_2)_{16}COOH$; but, depending on its method of preparation, it has mixed therewith varying amounts of palmitic acid. Trace amounts of other by-produced components such as ethylenically unsaturated acids, fats and oils may also be present. For the purposes of this invention component (c) is greater than 95 percent by weight, and preferably greater than 99 percent by weight, solid alkanoic acid having an average of at least 12 carbon atoms per molecule.

Component (c) is referred to as a stick-stabilizing component because its omission from the compositions of this invention results in a crystalline antiperspirant stick that "leaks", i.e. oozes fluid.

Component (d) is a polydiorganosiloxanepolyoxyalkylene copolymer containing at least one polydiorganosiloxane segment and at least one polyoxyalkylene segment. The polyoxyalkylene segments may be bonded to the polydiorganosiloxane segments with silicon-oxygen-carbon bonds and/or with silicon-carbon bonds. Although component (d) is not soluble in water and is therefore not subjected to vigorous hydrolysis in the compositions of this invention, it is preferred that the copolymer (d) have silicon-carbon bonding instead of the more hydrolyzable silicon-oxygen-carbon bonding joining the polyoxyalkylene segments to the polydiorganosiloxane segments.

The polydiorganosiloxane segments of the copolymer (d) consist essentially of siloxane units which are interlinked by Si-O-Si linkages and which have the formula

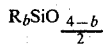

The value of b may range from 0 to 3 for said siloxane units with the provision that there is an average of approximately 2, i.e. from 1.9 to 2.1 R radicals for every silicon in the copolymer. Suitable siloxane units thus include $R_3SiO_{1/2}$, $R_2SiO_{2/2}$, $RSiO_{3/2}$, and $SiO_{4/2}$ siloxane units taken in such molar amounts so that b has an average value of approximately 2 in the copolymer. Said siloxane units may be arranged in linear, cyclic and/or branched fashion.

The R radicals of copolymer (d) may be any radical selected from the group consisting of methyl, ethyl, vinyl, phenyl, and a divalent radical bonding a polyoxyalkylene segment to the polydiorganosiloxane segment. At least 95 percent of all R radicals in the copolymer (d) are methyl radicals; preferably there is at least one methyl radical bonded to each silicon atom in (d). Divalent R radicals preferably contain no more than 6 carbon atoms. Examples of divalent R radicals include $-O-$, $-C_mH_{2m}O-$, $-C_mH_{2m}-$ and $-C_mH_{2m}CO_2-$ where m is an integer greater than zero.

Illustrative of the siloxane units that make up the polydiorganosiloxane segments of the copolymer (d) are the following, where Me denotes methyl and Q denotes said divalent R radical and bonded polyoxyalkylene segment: $R_3SiO_{1/2}$ units such as $Me_3SiO_{1/2}$, $Me_2(CH_2=CH)SiO_{1/2}$, $Me_2(C_6H_5)SiO_{1/2}$, $Me(C_6H_5)(CH_2=CH)SiO_{1/2}$, $Me_2(CH_3CH_2)SiO_{1/2}$, $Me_2QSiO_{1/2}$, $MeQ_2SiO_{1/2}$, $Q_3SiO_{1/2}$, $Q_2(CH_3CH_2)SiO_{1/2}$, and $Me(C_6H_5)(Q)SiO_{1/2}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2=CHSiO_{3/2}$, $CH_3CH_2SiO_{3/2}$ and $QSiO_{3/2}$; and $SiO_{4/2}$ units.

It is to be understood that copolymer (d) may comprise one or more of said polydiorganosiloxane segments. The number of and average molecular weight of the polydiorganosiloxane segments in the copolymer is related to the desired weight ratio, hereinafter described, of said segments in the copolymer. Preferably copolymer (d) comprises one polydiorganosiloxane segment having bonded thereto one or more polyoxyalklylene segments.

The polyoxyalkylene segments of the copolymer (d) consist essentially of oxyethylene units of the formula $-CH_2CH_2O-$, alone, or in combination with oxypropylene units of the formula $-CH_2CH(CH_3)O-$, an average of at least half of the oxyalkylene units in the polyoxyalkylene segments being oxyethylene units. Suitable emulsions of this invention are not formed when the polyoxyalkylene segments contain more than 50 mol percent of the relatively hydrophobic oxypropylene unit. The polyoxyalkylene segments thus correspond to the formula $\{-CH_2CH_2O-\}_p\{-CH_2CH(CH_3)O-\}_q$ wherein the oxyalkylene units may be arranged in any suitable fashion such as random, alternating and block. The average values of p and q are such that $p \geq q$ and the sum of $p+q$ is sufficient to provide an average molecular weight of at least 1,000 for the polyoxyalkylene segments. Preferably the average molecular weight of the polyoxyalkylene segments has a value of from 1,500 to 5,000.

The polyoxyalkylene segments of the copolymer (d) are bonded to the polydiorganosiloxane segments of said copolymer by at least one terminal portion of said polyoxyalkylene segment, said bonding being by way of a divalent R radical, hereinbefore described. It is to be understood that said bonding may be by both terminal portions of said polyoxyalkylene segment in those copolymers comprising more than one polydiorganosiloxane segments. Any terminal portion of the polyoxyalkylene segment of copolymer (d) that is not bonded to a polydiorganosiloxane segment is satisfied by a terminating radical. The type of said terminating radical is not critical and may be monovalent, thereby terminating one polyoxyalkylene segment, or polyvalent, thereby terminating more than one polyoxyalkylene segment. Said terminating radicals are made up of atoms selected from the group consisting of carbon, hydrogen, nitrogen, and oxygen. Illustrative of said terminating radical are hydrogen; hydroxyl; alkyl, such as methyl, ethyl, propyl, butyl; benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino such as dimethylamino.

The number of and average molecular weights of the segments in the copolymer (d) are such that the weight ratio of polydiorganosiloxane segments to polyoxyalkylene segments in copolymer (d) has a value of from 2 to 8, and preferably from 2.5 to 4.0. This weight ratio will insure that the copolymer (d) has a preferential solubility in the volatile liquid, a condition necessary for the formation of stable water-in-oil type emulsions of this invention.

The weight ratio of polydiorganosiloxane segments to polyoxyalkylene segments in copolymer (d) is calculated on the basis of the total weight of polydiorganosiloxane and the total weight of polyoxyalkylene that is joined in the copolymerization process. For example, if 100 parts by weight of polydiorganosiloxane is joined completely by an addition process, which utilizes silicon-bonded hydrogen radicals, with 20 parts by weight of polyoxyalkylene, said weight ratio of the resulting copolymer has a value of 5. Of course, if said complete joining is accomplished by a displacement reaction, involving a silicon-bonded hydrolyzable radical and resulting in the formation of a by-product, the weight ratio of polydiorganosiloxane to polyoxyalkylene in the resulting copolymer may not be identical with the weight ratio of the corresponding reactants, due to the loss of the weight of the displaced groups. The error introduced into the calculation of said weight ratio by ignoring the loss of said displaced groups is usually insignificant. That is to say, the weight ratio of polydiorganosiloxane to polyoxyalkylene in copolymer (d) may be calculated from the weight of reactants that react to form the copolymer or said weight ratio may be determined by suitable analysis of the resulting copolymer itself. Suitable analytical techniques such as elemental analysis, nuclear magnetic resonance spectroscopy, silicon substituent analysis and infra-red spectroscopy may be found in "Analysis of Silicones", A. Lee Smith, Ed., John Wiley and Sons, New York, 1974.

Herein, copolymer means either a block arrangement of segments such as denoted by the formulae $(AB)_c$, $A(BA)_c$ and $B(AB)_c$ or a pendant arrangement of segments such as $(AB_d)_c$ or combinations thereof wherein A denotes a polydiorganosiloxane segment, B denotes a polyoxyalkylene segment and c and d denote integers greater than zero and greater than one, respectively.

Copolymers (d) may be prepared by modifications of the well-known methods described in the polydiorganosiloxane-polyoxyalkylene copolymer art. The following patents are hereby incorporated by reference to show the preparation of polydiorganosiloxane-polyoxyalkylene copolymers: Haluska, U.S. Pat. Nos. 2,868,824; Haluska, Re 25,727; Bailey, 3,172,899; Pater, 3,234,252, Simmler, et al. 3,174,987; Bailey, et al., 3,562,786, 3,600,418 and 3,629,308; Holdstock, 3,629,165; and Gee et al., 4,122,029.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the copolymer (d).

Component (e) is an emulsion-stabilizing component selected from the group consisting of waxy esters and mixtures thereof with limited amounts of solid alkanols having at least 12 carbon atoms per molecule.

Component (e) is referred to as an emulsion-stabilizing component because its omission from the compositions of this invention or its dilution with more than three parts of solid alkanol per one part of waxy ester results in a molten composition which demonstrates very little resistance to separation in the molten state.

By waxy ester it is meant compounds of the formula $C_eH_{2e+1}CO_2C_fH_{2f+1}$ wherein e and f have values so that the ester is a solid below 20° C., and preferably below 40° C. Preferably the waxy ester is selected from the group of waxy esters which are widely used in the cosmetic art, such as spermaceti wax, cetyl palmitate, stearyl palmitate, beeswax and myricyl palmitate. The waxy ester may be a single waxy ester or a mixture of two or more of such waxy esters and may be of synthetic and/or natural origin.

It should be noted that although many waxy esters can be prepared in essentially pure form, they are usually used in the cosmetic art as mixtures. For example, natural used in the cosmetic art as mixtures. For example, natural spermaceti wax is predominantly cetyl palmitate; however it contains small amounts of cetyl alcohol; esters of lauric, stearic and myristic acid and esters of higher alcohols. Trace amounts of other esters may also be present, such as esters of long chain olefinically unsaturated acids, dicarboxylic acids and hydroxy acids.

The hardness of the stick compositions of this invention, which affects the glide, i.e. ease of application, and payout, i.e. rate of application, of the stick, is directly related to, among other parameters, the melting point of the waxy ester. For a desirable payout and glide the waxy ester preferably has a melting point between 20° C. and 60° C.; however, higher melting waxy esters may be mixed therewith in small amounts, particularly when the hardness of the stick is further controlled by varying other parameters which directly affect hardness, such as the amount and melting point of any alkanol that may be mixed with the waxy ester and the total amount of component (e) that is present in the composition.

Component (e) may consist solely of a waxy ester or the waxy ester may be mixed with up to three parts by weight, for every part by weight of the waxy ester, of a solid alkanol having at least 12 carbon atoms per molecule. Stability of the molten composition, hereinabove discussed, is not obtained when this weight ratio of solid alkanol to waxy ester is appreciably larger than 3. Any solid alkanol that is present in the waxy ester, such as impurity amounts of cetyl alcohol, contributes to the value of this ratio.

By solid it is meant that the alkanol has a melting point above 20° C., but, preferably, not above 60° C. Preferably any alkanol that is used is selected from the group of alkanols which are widely used in the cosmetic art, such as lauryl alcohol, myristyl alcohol, cetyl alcohol and stearyl alcohol.

The compositions of this invention consist essentially of 30 to 60 parts by weight of the aqueous solution of an astringent (a), dispersed in 40 to 70 parts by weight of a solid matrix consisting essentially of components (b) to (e), the total of the aqueous solution and the solid matrix being 100 parts by weight. In a preferred embodiment the aqueous solution of astringent consists of a 50/50 weight mixture of water and aluminum chlorhydrate and accounts for 40 to 50 parts by weight of the 100 parts by weight of the compositions of this invention.

The solid matrix, amounting to 40 to 70 parts by weight, for every 100 parts by weight of the aqueous component (a) plus said matrix, consists essentially of 18 to 30 parts by weight of the volatile fluid (b), 1 to 5 parts by weight of the polydiorganosiloxane-polyoxyalkylene copolymer (d) and 21 to 35 parts by weight of the mixture of stick-forming components (c) plus (e). In the preferred embodiment above the solid matrix amounts to 50 to 60 parts by weight.

The mixture of stick-forming components consists essentially of from 1 to 5, preferably 2 to 4, parts by weight of the solid alkanoic acid (c) and from 20 to 30 parts by weight of component (e), i.e. the waxy ester or mixture thereof with a solid alkanol, and accounts for from 21 to 35 parts by weight for every 100 parts by weight of components (a) to (e).

The hardness of an antiperspirant stick composition of this invention is increased with increasing amounts of component (e) and by increasing the weight ratio of the solid alkanol to waxy ester in component (e) within the limits delineated above. Said hardness is decreased with increasing amounts of the solid alkanoic acid.

The separation-stability of the molten water-in-oil type emulsion from which the antiperspirant stick composition is cast is directly related to the amount of waxy ester that is present in the compositions of this invention.

The compositions of this invention may further comprise small amounts of non-essential components which are used in the cosmetic art. Examples of such components include colorants; perfumes, further hardness-controlling components, such as mineral oil and hydrocarbon waxes; non-volatile organopolysiloxanes, such as polydimethylsiloxane fluids having a viscosity of from 10 to 10,000 millipascal-seconds at 25° C., and surfactants, such as those used in the compositions of Gee et al., U.S. Pat. No. 4,122,029 and of the above-mentioned Keil U.S. Pat. Application cofiled herewith.

The method of preparation of the antiperspirant stick compositions of this invention is not critical and may be accomplished in any suitable fashion. The best preparative method currently known is to form a warm solution (60°–75° C.) of the proper amounts of (b) through (e) and thereafter emulsify a proper amount of warm component (a) therein using standard emulsifying procedures. Non-essential components may be admixed at the desired time. The resulting emulsion has long term stability at the temperatures commonly used during preparing, holding and pouring the emulsion. On cooling, the emulsion solidifies to a uniform, non-leaking antiperspirant stick of the dry-feeling type.

Now in order that those skilled in the art may better understand how the present invention can be practiced, the following specific components and examples are disclosed for purposes of illustrating and not limiting the invention. All percentages and parts are by weight, and all pressures were measured in millimeters of mercury and were converted to kilopascals by multiplying by 0.1333224 and rounding off.

Polydiorganosiloxane-polyoxyalkylene Copolymer—The polydiorganosiloxane-polyoxyalkylene copolymer that was used in the following examples, and designated as "Copolymer" in the Table was prepared from a trimethylsiloxane-endblocked polydimethylsiloxane having a molecular weight of approximately 30,000 and having an average of approximately 4 of its dimethylsiloxane units replaced with methylhydrogensiloxane units, and a random equimolar polyglycol copolymer of ethylene oxide and propylene oxide having an average molecular weight of approximately 2550 and having allyloxy endgroups on one end and acetoxy endgroups on the other end. Two hundred twenty grams of the siloxane, 80.76 grams of the polyglycol and 75.19 grams of isopropanol were mixed and heated to reflux under dry nitrogen in a flask and the resulting solution was catalyzed with 0.15 ml. of a 1 molar solution of $H_2PtCl_6$ in isopropanol. The reaction mixture was heated at reflux for one hour and then devolatilized at 110° C. and 1.33 kilopascals pressure. The polydimethylsiloxane-polyoxyalkylene copolymer product had a siloxane/oxyalkylene weight ratio of approximately 2.7 and —$CH_2CH_2CH_2O$— divalent radicals bonding the polyoxyalkylene portion to the polydimethylsiloxane portion by way of a silicon-carbon bond.

Voltile Liquid—The volatile liquid that was used in the following examples and designated as "Volatile Liquid" in the Table was a commerically available mixture of a major amount of octamethylcyclotetrasiloxane and minor amounts of larger cyclic dimethylsiloxanes.

50% ACH—The antiperspirant astringent ingredient that was used in the following examples, and designated "50% ACH" in the Table was a 50 percent by weight solution of aluminum chlorhydrate in water.

Spermaceti Wax—Two types of synthetic spermaceti wax were used in the compositions. Spermaceti wax (A) was a synthetic spermaceti wax having a melting range of 51° to 55° C., an iodine value not exceeding 1.0 and a saponification value of from 109 to 117 and containing the same components as natural spermaceti wax. Spermaceti wax (B) was a synthetic spermaceti wax which meets National Formulary (N.F.) specifications and had a melting range of 43° to 47° C., an iodine value not exceeding 1.0 and a saponification value of from 109 to 117.

Compositions—The compositions noted in the Table were prepared by dissolving one part of the polydiorganosiloxane-polyoxyalkylene copolymer in 9 parts of the volatile liquid mixture of cyclic polydimethylsiloxanes to form a stock solution and blending with a suitable portion thereof, at 60°-75° C., the indicated amounts of stearic acid, spermaceti wax, and solid alkanol and sufficient additional volatile liquid to obtain the total amounts of components indicated in the Table. The indicated amount of warm 50% ACH was then slowly added to the warm blend of (b) through (e) while the latter was being agitated in an Eppenbach brand homogenizer. The resulting emulsion was rated from Excellent to Unstable based on a visual examination of its degree of "color", i.e. opalescence. Unstable emulsions have no "color".

The molten compositions were poured into a stick mold and were allowed to cool to room temperature. Sticks which crystallized on cooling also oozed fluid, i.e. leaked. Sticks which formed a non-crystalline solid matrix were dry, i.e. did not leak. Dry sticks were further ranked, qualitatively, with respect to hardness, by rubbing them on the palmar side of the wrist and noting the glide and payout that occurred.

TABLE

| Composition Number[1] | Components - Parts | | | | | | Properties | |
|---|---|---|---|---|---|---|---|---|
| | 50% ACH | Volatile Liquid | Stearic Acid | Copolymer | Spermaceti Wax[2] | Stearyl Alcohol | Emulsion | Stick |
| 1 | 50 | 26.00 | 2.5 | 1.50 | 20.00(A) | 0 | Excellent | Dry |
| 2 | 50 | 23.75 | 2.5 | 1.25 | 22.50(A) | 0 | Excellent | Dry, Hardest |
| 3 | 50 | 23.75 | 2.5 | 1.25 | 11.25(A) | 11.25 | Good | Dry, Firm |
| 4 | 50 | 23.75 | 2.5 | 1.25 | 5.70(A) | 16.80 | Acceptable | Dry, Harder |
| 5 | 50 | 23.75 | 2.5 | 1.25 | 22.50(B) | 0 | Excellent | Dry, Softest |
| 6 | 50 | 23.75 | 2.5 | 1.25 | 11.25(B) | 11.25 | Good | Dry, Softer |
| 7 | 50 | 23.75 | 2.5 | 1.25 | 5.70(B) | 16.80 | Acceptable | Dry, Firm |
| 8 | 50 | 21.25 | 2.5 | 1.25 | 25.00(B) | 0 | Excellent | Dry |
| 9a | 50 | 23.75 | 0 | 1.25 | 25.00(A) | 0 | Excellent | Leak |
| 9b | 50 | 23.75 | 2.5 | 1.25 | 0 | 22.5[3] | Unstable | Dry |
| 9c[4] | 50 | 26.00 | 0 | 1.50 | 21.50(A) | 0 | Acceptable | Leaked |

[1]Compositions 9a, 9b, 9c are for comparison purposes only.
[2](A) Synthetic spermaceti wax, m.p. 51°-55° C.; (B) Synthetic spermaceti wax N.F., m.p. 43°-47° C.
[3]Cetyl alcohol
[4]Also contains 1.5 parts of a water-in-oil surfactant having an HLB value of 8.6.

That which is claimed is:

1. An antiperspirant stick composition consisting essentially of
(a) 30 to 60 parts by weight of an aqueous solution of an astringent agent as a discontinuous phase, dispersed in a solid matrix consisting essentially of
(b) 18 to 30 parts by weight of a volatile liquid having a normal boiling point of less than 250° C. selected from the group consisting of methylsiloxane fluids having the average unit formula

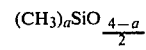

wherein a has an average value of from 2 to 3, inclusive, and paraffinic hydrocarbon fluids, (c) 1 to 5 parts by weight of a component selected from the group consisting of solid alkanoic acids having at least 12 carbon atoms per molecule, (d) 1 to 5 parts by weight of a polydiorganosiloxanepolyoxyalkylene copolymer containing at least one polydiorganosiloxane segment and at least one polyoxyalkylene segment, said polydiorganosiloxane segment consisting essentially of

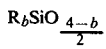

siloxane units wherein b has a value of from 0 to 3, inclusive, there being an average value of approximately 2 R radicals per silicon for all siloxane units in the copolymer, and R denotes a radical selected from the group consisting of methyl, ethyl vinyl, phenyl and a divalent radical bonding said polyoxyalkylene segment to the polydiorganosiloxane segment, at least 95 percent of all R radicals being methyl; and said polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8 and (e) 20 to 30 parts by weight of a component selected from the group consisting of waxy esters and a mixture of one part by weight of a waxy ester with up to 3 parts by weight of a solid alkanol having at least 12 carbon atoms per molecule, the total of (a) plus (b) plus (c) plus (d) plus (e) being 100 parts by weight.

2. The antiperspirant stick composition of claim 1 wherein component (c) is stearic acid and comprises 2 to 4 percent by weight of the total weight of components (a) to (e).

3. The antiperspirant stick composition of claim 2 wherein component (e) comprises 20 to 25 percent by weight of the total of components (a) to (e) and consists of 75 to 100 percent by weight of spermaceti wax and 0 to 25 percent by weight stearyl alcohol based on the weight of (e).

4. The antiperspirant stick composition of claims 1, 2 or 3 wherein the volatile liquid is a mixture of cyclic dimethylsiloxanes wherein a major amount is octamethylcyclotetrasiloxane.

5. The antiperspirant stick composition of claim 4 wherein the aqueous solution of an astringent consists of equal weights of water and aluminum chlorhydrate and comprises from 40 to 50 percent by weight of the total weight of components (a) to (e).

* * * * *

UNITED STATES PATENT AND TRADEMARK OFFICE
CERTIFICATE OF CORRECTION

PATENT NO. : 4,265,878
DATED : May 5, 1981
INVENTOR(S) : Joseph W. Keil

It is certified that error appears in the above-identified patent and that said Letters Patent are hereby corrected as shown below:

ABSTRACT, line 9; the word reading "clopolydimthylsiloxanes" should read "clopolydimethylsiloxanes".

In Column 10, line 45; under the column heading Stick the word reading "Leak" should read "Leaked".

Signed and Sealed this

Eighth Day of September 1981

[SEAL]

Attest:

GERALD J. MOSSINGHOFF

Attesting Officer     Commissioner of Patents and Trademarks